United States Patent [19]

Spivack et al.

[11] Patent Number: 4,524,166
[45] Date of Patent: Jun. 18, 1985

[54] PRIMARY OR SECONDARY AMINO SUBSTITUTED DIBENZO DIOXAPHOSPHEPINS AND DIOXAPHOSPHOCINS

[75] Inventors: John D. Spivack; Stephen D. Pastor, both of Spring Valley, N.Y.

[73] Assignee: Ciba-Geigy Corporation, Ardsley, N.Y.

[21] Appl. No.: 651,185

[22] Filed: Sep. 14, 1984

Related U.S. Application Data

[63] Continuation-in-part of Ser. No. 437,930, Nov. 1, 1982, abandoned.

[51] Int. Cl.³ .................... C07F 9/15; C08G 59/02; C08G 63/68; C08G 69/42; C08K 5/32
[52] U.S. Cl. .................... 524/117; 523/421; 524/119; 528/72; 528/108; 528/287; 528/313; 528/321; 260/927 R; 260/936
[58] Field of Search .................... 524/117, 119; 260/927 R, 936; 523/421; 528/72, 108, 287, 313, 321; 549/219

[56] References Cited

U.S. PATENT DOCUMENTS

| | | | |
|---|---|---|---|
| 4,196,117 | 1/1980 | Spivack | 524/119 |
| 4,252,750 | 2/1981 | Buysch et al. | |
| 4,259,492 | 3/1981 | Rasberger | 524/117 |
| 4,288,391 | 9/1981 | Spivack | 260/927 R |
| 4,301,061 | 11/1981 | Rasberger | 524/117 |
| 4,318,845 | 3/1982 | Spivack et al. | 524/117 |
| 4,322,527 | 3/1982 | Rasberger et al. | 260/927 R |
| 4,348,495 | 9/1982 | Buysch et al. | |
| 4,351,759 | 9/1982 | Spivack et al. | 524/117 |
| 4,374,219 | 2/1983 | Spivack et al. | 524/117 |

Primary Examiner—Veronica P. Hoke
Attorney, Agent, or Firm—Luther A. R. Hall; Harry Falber

[57] ABSTRACT

Primary or secondary amino substituted hindered phosphites of the formula

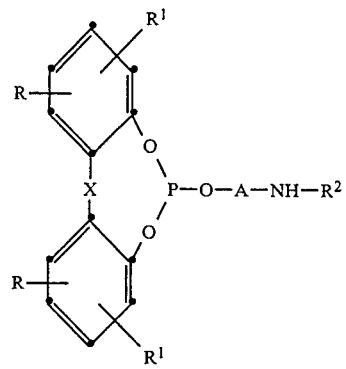

are prepared by reaction of the appropriate phosphorus and phenol compounds, said hindered phosphites being useful as stabilizers of organic polymers and lubricating oils.

25 Claims, No Drawings

PRIMARY OR SECONDARY AMINO SUBSTITUTED DIBENZO DIOXAPHOSPHEPINS AND DIOXAPHOSPHOCINS

This is a continuation-in-part of application Ser. No. 437,930, filed on Nov. 1, 1982 now abandoned.

Organic polymeric materials such as plastics and resins, and lubricating and mineral oils are subject to thermal, oxidative and photodegradation. A great variety of stabilizers are known in the art for stabilizing various substrates. Their effectiveness varies depending on the causes of degradation and the substrate stabilized. During the course of this work, it was discovered that stabilizers that are very effective long term antioxidants are relatively poor process stabilizers and do not protect the substrate against thermal degradation for a short time at relatively high process temperatures. Many stabilizers are relatively incompatible with the substrates which causes problems during the life of a product and lessens the stabilizer's effectiveness. Some stabilizers are either too volatile or thermally or hydrolytically unstable to be practical as commercial stabilizers.

The phosphites of this invention possess an unusual combination of desirable properties as compared to the prior art phosphites which makes these compounds particularly effective and useful as stabilizers.

Phosphites are disclosed in a number of publications. U.S. Pat. No. 4,196,117 discloses biphenyl-cyclic phosphites wherein the phosphorus atom is substituted by O- or S-hydrocarbyl or a hydrocarbyl biphenyl cyclic phosphite group. Soviet Union U.S. Pat. Nos. 378,389, 429,070 and 440,390 disclose the stabilization of various polymers with organic phosphites or mixtures including said phosphites wherein the phosphites are methylene-bisphenyl cyclic phosphites. Additional 1,1'-biphenyl-2,2'-diyl phosphites are disclosed in Chemical Abstracts, 68, 12597s (1968), 73, 15657a (1970) and 75, 130242q(1971). These various compounds are indicated to be stabilizers of various polymers. However, the instant compounds are significantly more effective as process stabilizers, as color stabilizers and in resistance to hydrolysis.

In addition, alkanolamine phosphites and the stabilization of vinyl and vinylidene resins therewith are disclosed in U.S. Pat. No. 2,841,607. Other alkanolamine esters of cyclic phosphites are disclosed in U.S. Pat. Nos. 4,318,845, and 4,374,219. More particularly, the compounds in the latter patents are tertiary amino-substituted cyclic phosphites. It is to be noted, however, that these prior phosphites are distinct in structure from the instant compounds.

U.S. Pat. No. 4,259,492 pertains to dioxaphosphepines wherein the phosphorus atom is linked directly to a nitrogen atom which nitrogen is derived from a primary or secondary amine. The dioxaphosphepines of this patent are phosphonamides, not phosphites as are the instant compounds.

Accordingly, it is the primary object of this invention to provide biphenyl cyclic phosphite compounds which exhibit improved process stabilization performance as contrasted with previously known phosphite compounds.

The instant phosphite compounds differ from the closest compounds of the prior art, namely those of U.S. Pat. Nos. 4,318,845 and 4,374,219 by being derived from primary or secondary aminoalcohols so that in every case the nitrogen atom in the instant compounds is attached to at least one hydrogen atom.

While the remainder of the instant compounds containing the hindered phosphite moiety provides important stabilization effects such as color stabilization, resistance to hydrolysis and superior processing stabilization efficacy shared by the compounds of U.S. Pat. Nos. 4,318,845 and 4,374,219, the presence of the one or two hydrogen atoms on the nitrogen atom of the instant compounds provides an active site for selected chemical reactions not possible with the prior art compounds having only tertiary amino groups.

These active sites allow for the chemical incorporation of the instant compounds into a polymer to be stabilized during cure, for example with polyurethanes, polyesters, polyamides or polyepoxides.

That is with such polymers or more appropriately with their precursors the instant compounds having at least one hydrogen on the nitrogen atom may react with the isocyanate, acid chloride or epoxide precursor to attach the instant compound firmly to the polymer in a terminal and/or pendant position.

Various other objects and advantages of this invention will become evident from the following description thereof.

The compounds of this invention correspond to the formula:

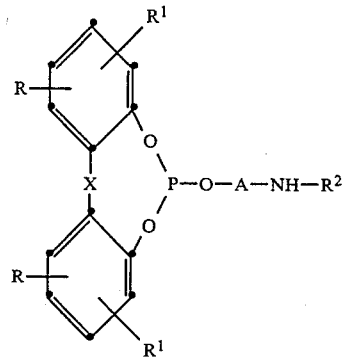

wherein

R and $R^1$ independently are hydrogen, alkyl of 1 to 18 carbon atoms, cycloalkyl of 5 to 6 carbon atoms, phenyl or substituted phenyl of 7 to 24 carbon atoms;

A is alkylene of 1 to 6 carbon atoms or cycloalkylene of 5 to 6 carbon atoms;

X is a direct bond or alkylidene of 1 to 12 carbon atoms; and $R^2$ is hydrogen, alkyl of 1 to 12 carbon atoms, or the group

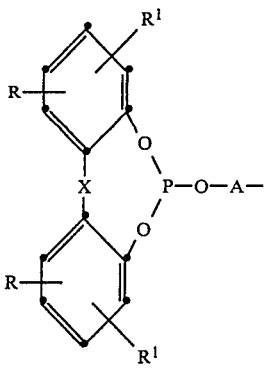

Preferred compounds within the above structure are those wherein R is in the ortho position to the phosphite oxygen in each of the pheny rings.

The R and $R^1$ groups are preferably straight-chain or branched alkyl with 4 to 8 carbon atoms, such as n-butyl, sec-butyl, tert-butyl, tert-pentyl, 2-ethylhexyl, n-octyl and tert-octyl. The groups tert-butyl, tert-pentyl and tert-octyl are especially preferred. Also especially preferred is for the $R^1$ group to be in the para position to oxygen, particularly if $R^1$ is tert-alkyl.

Although $R^1$ can be hydrogen or alkyl of 1 to 18 carbons, preferably it is an alkyl group of 1 to 8 carbon atoms, either straight-chain or branched-chain. Especially preferred is tert-alkyl of 4 to 8 carbon atoms.

The substituents on the phenyl in R and $R^1$ include alkyl of 1 to 18 carbon atoms.

X is preferably lower alkylidene of the formula

wherein $R^3$ and $R^4$ are independently hydrogen or alkyl of 1 to 7 carbon atoms, provided that the number of carbon atoms does not exceed 12.

$R^2$ is preferably hydrogen, alkyl of 1 to 4 carbon atoms or the indicated phosphite group.

The phosphites of this invention can be prepared by reacting an alkylated 2,2'-biphenol or an alkylated 2,2'-alkylidene-bis-phenol with phosphorus trichloride optionally in a solvent to give the corresponding phosphorochlorodite which in turn is reacted with an amino alkoxide or alkanol amine to yield the desired product. The solvent is preferably aromatic, such as benzene, toluene, xylene and the like. The reaction temperature ranges from room temperature to the reflux temperature of the reaction medium. The preferred method for preparing the compounds of this invention involves reacting the phosphorochlorodite with an appropriate alkanolamine in the presence of a proton acceptor such as a tertiary amine, for example, triethylamine or pyridine.

The starting materials needed to prepare these phosphites are items of commerce or can be prepared by known methods.

The alkanolamines used to prepare the compounds correspond to the formulae $R^2$—NH—A—OH or

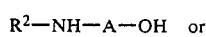

NH—(A—OH)$_2$ wherein $R^2$ is hydrogen or alkyl of 1 to 12 carbon atoms, and A is as previously defined.

Preferred alkanolamines include ethanolamine, diethanolamine, N-methyl ethanolamine, N-ethyl ethanolamine and N-tert-butyl ethanolamine.

An analogous synthetic method would involve substituting alkali metal hydroxides or alkali metal carbonates for the tertiary amines in the synthetic scheme. The reaction sequences can be conducted to yield the compounds of this invention without isolation of the intermediate chlorodite.

Compounds of this invention are effective in stabilizing organic materials such as plastics, polymers and resins in addition to mineral and synthetic fluids such as lubricating oils, circulating oils, etc.

The compounds of the invention are particularly useful as stabilizers, especially for the protection of polyolefins, for instance, polyethylene, polypropylene, polyisobutylene, poly(butene-1), poly(pentenel-1), poly(3-methylbutene-1), poly(4-methyl-pentene-1), various ethylene-propylene copolymers and the like.

Other substrates in which the compounds of this invention are particularly useful are polystyrene, including impact polystyrene, ABS resin, SBR, isoprene, as well as natural rubber, polyesters including polyethylene terephthalate and polybutylene terephthalate, including copolymers.

Polyurethanes, polycarbonates, polyamides such as nylon 6, 6/6 and the like as well as copolyamides and polysulfones are also stabilized.

The primary and secondary amino-substituted cyclic phosphites of this invention are also valuable as chemical intermediates. Thus, unlike tertiary compounds which have no reactive hydrogen, these primary and secondary compounds can undergo a variety of substitution and addition reactions. Typical reactions include (1) Michael addition, (2) addition to aldehydes and ketones, (3) acylation to form amides, (4) sulfonation to sulfonamides, (5) alkylation and (6) reaction with epoxides. A discussion of amine reactions can be found in I. O. Sutherland, Ed., "Comprehensive Organic Chemistry," Pergamom Press, New York, 1979, Vol. 2, pp. 38–42, and J. March, "Advanced Organic Chemistry," McGraw-Hill, New York, 1977.

Polymers having groups, terminal or pendant, which can react with active hydrogen atoms are particularly well stabilized by the instant phosphites since the instant phosphites are chemically bonded into the polymer and are thus able to provide more permanent, non-extractable stabilization protection to the polymer. Such polymers are particularly the polyurethanes, polyesters, polyamides, and epoxy resins, especially polyurethanes and epoxy resins.

In general, polymers which can be stabilized include:

1. Polymers of monoolefins and diolefins, for example polyethylene (which optionally can be crosslinked), polypropylene, polyisobutylene, polybutene-1, polymethylpentene-1, polyisoprene or polybutadiene, as well as polymers of cycloolefins, for instance of cyclopentene or norbornene.

2. Mixtures of the polymers mentioned under (1), for example mixtures of polypropylene with polyethylene or with polyisobutylene.

3. Copolymer of monoolefins and diolefins with each other or with other vinyl monomers, such as, for example, ethylene/propylene, propylene/butene-1, propylene/isobutylene, ethylene/butene-1, propylene/butadiene, isobutylene/isoprene, ethylene/ethyl acrylate, ethylene/alkyl methacrylates, ethylene/vinyl acetate or ethylene/acrylic acid copolymers and their salts (ionomers) and terpolymers of ethylene with propylene and a diene, such as hexadiene, dicyclopentadiene or ethylidene norbornene.

4. Polystyrene.

5. Random copolymers of styrene of α-methylstyrene with dienes or acrylic derivatives, such as, for example, styrene/butadiene, styrene/acrylonitrile, styrene/alkyl methacrylates, styrene/acrylonitrile/methyl acrylate; mixtures of high impact strength from styrene copolymers and another polymer, such as, for example, from a polyacrylate, a diene polymer or an ethylene/propylene/diene terpolymer; and block copolymers of styrene, such as, for example, styrene/butadiene/styrene, styrene/isoprene/styrene, styrene/ethylene/butylene/styrene or styrene/ethylene/propylene/styrene.

6. Graft copolymers of styrene, such as, for example, styrene on polybutadiene, styrene and acrylonitrile on polybutadiene, styrene and alkyl acrylates or methacrylates on polybutadiene, styrene and acrylonitrile on ethylene/propylene/diene terpolymers, styrene and acrylonitrile on polyacrylates or polymethacrylates, styrene and acrylonitrile on acrylate/butadiene copolymers, as well as mixtures thereof with the copolymers listed under (5), for instance the copolymer mixtures known as ABS-, MBS-, ASA- or AES-polymers.

7. Halogen-containing polymers, such as polychloroprene, chlorinated rubbers, chlorinated or sulfochlorinated polyethylene, polymers from halogen-containing vinyl compounds, as for example, polyvinyl chloride, polyvinylidene chloride, polyvinyl fluoride, polyvinylidene fluoride, as well as copolymers thereof, as for example, vinyl chloride/vinylidene chloride, vinyl chloride/vinyl acetate or vinylidene chloride/vinyl acetate copolymers.

8. Polymers which are derived from α,β-unsaturated acids and derivatives thereof, such as polyacrylates and polymethacrylates, polyacrylamides and polyacrylonitrile.

9. Copolymers from the monomers mentioned under (8) with each other or with other unsaturated monomers, such as, for instance, acrylonitrile/butadiene, acrylonitrile/alkyl acrylate or acrylonitrile/vinyl chloride copolymers or acrylonitrile/alkyl methacrylate/butadiene terpolymers.

10. Polymers which are derived from unsaturated alcohols and amines, or acyl derivatives thereof or acetals thereof, such as polyvinyl alcohol, polyvinyl acetate, polyvinyl stearate, polyvinyl benzoate, polyvinyl maleate, polyvinylbutyral, polyallyl phthalate or polyallylmelamine.

11. Homopolymers and copolymers of cyclic ethers, such as polyalkylene glycols, polyethylene oxide, polypropylene oxide or copolymers thereof with bis-glycidyl ethers.

12. Polyacetals, such as polyoxymethylene and those polyoxymethylenes which contain ethylene oxide as a comonomer.

13. Polyphenylene oxides and sulfides.

14. Polyurethanes which are derived from polyethers, polyesters or polybutadienes with terminal hydroxyl groups on the one side and aliphatic or aromatic polyisocyanates on the other side, as well as precursors thereof.

15. Polyamides and copolyamides which are derived from diamines and dicarboxylic acids and/or from aminocarboxylic acids of the corresponding lactams, such as polyamide 4, polyamide 6, polyamide 6/6, polyamide 6/10, polyamide 11, polyamide 12, poly-2,4,4-trimethylhexamethylene terephthalamide or poly-m-phenylene isophthalamide, as well as copolymers thereof with polyethers, such as for instance, with polyethylene glycol, polypropylene glycol or polytetramethylene glycols.

16. Polyureas, polyimides and polyamide-imides.

17. Polyesters which are derived from dicarboxylic acids and dialcohols and/or from hydroxycarboxylic acids or the corresponding lactones, such as polyethylene terephthalate, polybutylene terephthalate, poly-1,4-dimethylolcyclohexane terephthalate and polyhydroxybenzoates as well as block copolyether-esters derived from polyethers having hydroxyl end groups.

18. Polycarbonates.

19. Polysulfones and polyethersulfones.

20. Crosslinked polymers which are derived from aldehydes on the one hand and phenols, ureas and melamines on the other hand, such as phenol/formaldehyde resins, urea/formaldehyde resins and melamine/formaldehyde resins.

21. Drying and non-drying alkyd resins.

22. Unsaturated polyester resins which are derived from copolyesters of saturated and unsaturated dicarboxylic acids with polyhydric alcohols and vinyl compounds as crosslinking agents, and also halogen-containing modifications thereof of low flammability.

23. Thermosetting acrylic resins, derived from substituted acrylic esters, such as epoxy-acrylates, urethane-acrylates or polyester-acrylates.

24. Alkyd resins, polyester resins or acrylate resins in admixture with melamine resins, urea resins, polyisocyanates or epoxide resins as crosslinking agents.

25. Crosslinked epoxide resins which are derived from polyepoxides, for example from bis-glycidyl ethers or from cycloaliphatic diepoxides and aromatic diepoxides.

26. Natural polymers, such as cellulose, rubber, gelatin and derivatives thereof which are chemically modified in a polymer-homologous manner, such as cellulose acetates, cellulose propionates and cellulose butyrates, or the cellulose ethers, such as methylcellulose.

27. Naturally occurring and synthetic organic materials which are pure monomeric compounds or mixtures of such compounds, for example mineral oils, animal and vegetable fats, oils and waxes, or oils, fats and waxes based on synthetic esters (e.g. phthalates, adipates, phosphates or trimellithates) and also mixtures of synthetic esters with mineral oils in any weight ratios, which materials may be used as plasticizer for polymers or as textile spinning oils, as well as aqueous emulsions of such materials.

28. Aqueous emulsions of natural or synthetic rubber, e.g. natural latex or latices of carboxylated styrene/butadiene copolymers.

In general, the stabilizers of this invention are employed in from about 0.01 to about 5% by weight of the stabilized composition, although this will vary with the particular substrate and application. An advantageous range is from about 0.05 to about 2%, and especially 0.1 to about 1%.

The stabilizers of the instant invention may readily be incorporated into the organic polymers by conventional techniques, at any convenient stage prior to the manufacture of shaped articles therefrom. For example, the stabilizer may be mixed with the polymer in dry powder form, or a suspension or emulsion of the stabilizer may be mixed with a solution, suspension, or emulsion of the polymer. The stabilized polymer compositions of the invention may optionally also contain various conventional additives, such as the following:

1. Antioxidants 1.1 Simple 2.6-dialkylphenols, such as, for example, 2,6-di-tert.-butyl-4-methylphenol, 2-tert.-butyl-4,6-dimethylphenol, 2,6-di-tert.-butyl-4-methoxymethylphenol and 2,6-di-octadecyl-4-methylphenol.

1.2. Derivatives of alkylated hydroquinones, such as, for example, 2,5-di-tert.-butyl-hydroquinone, 2,5-di-tert.-amyl-hydroquinone, 2,6-di-tert.-butyl-hydroquinone, 2,6-di-tert.-butyl-4-hydroxy-anisole, 3,5-di-tert.-butyl-4-hydroxy-anisole, tris-(3,5-di-tert.-butyl-4-hydroxyphenyl)phosphite, 3,5-di-tert.-butyl-4-hydroxyphenyl stearate and bis-(3,5-di-tert.-butyl-4-hydroxyphenyl)adipate.

1.3. Hydroxylated thiodiphenyl ethers, such as, for example, 2,2'-thio-bis-(6-tert.-butyl-4-methylphenol), 2,2'-thio-bis-(4-octylphenol), 4,4'-thio-bis-(6-tert.-butyl-3-methylphenol), 4,4'-thio-bis-(3,6-di-sec.-amylphenol), 4,4'-thio-bis-(6-tert.-butyl-2-methylphenol) and 4,4'-bis-(2,6-dimethyl-4-hydroxy-phenyl)disulphide.

1.4. Alkylidene-bisphenols, such as, for example, 2,2'-methylene-bis-(6-tert.-butyl-4-methylphenol), 2,2'-methylene-bis-(6-tert.-butyl-4-ethylphenol), 4,4'-methylene-bis-(6-tert.-butyl-2-methylphenol), 4,4'-methylene-bis-(2,6-di-tert.-butyl-phenol), 2,6-di-(3-tert.-butyl-5-methyl-2-hydroxybenzyl)-4-methylphenol, 2,2'-methylene-bis-[4-methyl-6-(α-methylcyclohexyl)-phenol], 1,1-bis-(3,5-dimethyl-2-hydroxyphenyl)-butane, 1,1-bis-(5-tert.-butyl-4-hydroxy-2-methylphenyl)-butane, 2,2-bis-(3,5-di-tert.-butyl-4-hydroxyphenyl)-propane, 1,1,3-tris-(5-tert.-butyl-4-hydroxy-2-methylphenyl)-butane, 2,2-bis-(5-tert.-butyl-4-hydroxy-2-methylphenyl)-4-n-dodecylmercaptobutane, 1,1,5,5-tetra-(5-tert.-butyl-4-hydroxy-2-methylphenyl)-pentane and ethylene glycol bis-[3,3-bis-(3'-tert.-butyl-4'-hydroxyphenyl)-butyrate].

1.5. O-, N- and S-benzyl compounds, such as, for example, 3,3',5,5'-tetra-tert.-butyl-4,4'-dihydroxydibenzyl ether, octadecyl 4-hydroxy-3,5-dimethylbenzyl-mercaptoacetate, tris-(3,5-di-tert.-butyl-4-hydroxybenzyl)-amine and bis-(4-tert.-butyl-3-hydroxy-2,6-dimethylbenzyl)dithioterephthalate.

1.6. Hydroxybenzylated malonates, such as, for example, dioctadecyl 2,2-bis-(3,5-di-tert.-butyl-2-hydroxybenzyl)-malonate, dioctadecyl 2-(3-tert.-butyl-4-hydroxy-5-methylbenzyl)-malonate, di-dodecylmercapto-ethyl 2,2-bis-(3,5-di-tert.-butyl-4-hydroxybenzyl)-malonate and di-[4-(1,1,3,3-tetramethylbutyl)-phenyl]2,2-bis-(3,5-di-tert.-butyl-4-hydroxybenzyl)-malonate.

1.7. Hydroxybenzyl-aromatic comounds, such as, for example, 1,3,5-tris-(3,5-di-tert.-butyl-4-hydroxybenzyl)-2,4,6-trimethylbenzene, 1,4-bis-(3,5-di-tert.-butyl-4-hyroxybenzyl)-2,3,5,6-tetramethylbenzene and 2,4,6-tri-(3,5-di-tert.-butyl-4-hydroxybenzyl)-phenol.

1.8. s-Triazine compounds, such as, for example, 2,4-bis-octylmercapto-6-(3,5-di-tert.-butyl-4-hydroxyanilino)-s-triazine, 2-octylmercapto-4,6-bis-(3,5-di-tert.-butyl-4-hydroxyanilino)-s-triazine, 2-octylmercapto-4,6-bis-(3,5-di-tert.-butyl-4-hydroxyphenoxy)-s-triazine, 2,4,6-tris-(3,5-di-tert.-butyl-4-hydroxyphenoxy)-S-triazine, 2,4,6-tris-(3,5-di-tert.-butyl-4-hydroxyphenylethyl)-s-triazine and 1,3,5-tris-(3,5-di-tert.-butyl-4-hydroxybenzyl)isocyanurate.

9. Amides of β-(3,5-di-tert.-butyl-4-hydroxyphenyl)-propionic acid, such as, for example, 1,3,5-tris-3,5-di-tert.-butyl-4-hydroxyphenyl-propionyl)-hexahydro-s-triazine and N,N'-di-(3,5-di-tert.-butyl-4-hydroxyphenyl-propionyl)-hexamethylenediamine. N,N'-bis-β-(3,5-di-t-butyl-4-hydroxyphenyl-propionyl)-hydrazine.

1.10. Esters of β-(3,5-di-tert.-butyl-4-hydroxyphenyl)propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, triethylene glycol, thiodiethylene glycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo-[2,2,2]octane.

1.11. Esters of β(5-tert.-butyl-4-hydroxy-3-methylphenyl)propionic acid with monohydric or polyhydric alcohols, such as, for example, with methanol, ethanol, octadecanol, 1,6-hexanediol, 1,9-nonanediol, ethylene glycol, 1,2-propanediol, diethylene glycol, triethylene glycol, thiodiethylene glycol, neopentylglycol, pentaerythritol, 3-thia-undecanol, 3-thia-pentadecanol, trimethylhexanediol trimethyolethane, trimethylolpropane, tris-hydroxyethyl isocyanurate and 4-hydroxymethyl-1-phospha-2,6,7-trioxabicyclo[2,2,2]octane.

1.12. Esters of 3,5-di-tert.-butyl-4-hydroxyphenylacetic acid with monohydric or polyhydric alcohols, such as, for example, with methanol, ethanol, octadecanol, 1,6-hexanediol, 1,9-nonanediol, ethylene glycol, 1,2-propanediol, diethylene glycol, thiodiglycol, neopentylglycol, pentaerythritol, 3-thia-undecanol, 3-thia-pentadecanol, trimethylhexanediol, trimethylolethane, trimethylolpropane, tris-hydroxyethyl isocyanurate and 4-hydroxymethyl-1-phospha-2,6,7-trioxabicyclo[2,2,2]-octane, especially the tetra-bis ester of pentaerythritol.

1.13. Benzylphosphonates, such as, for example, dimethyl 3,5-di-tert.-butyl-4-hydroxybenzyl-phosphonate, diethyl 3,5-di-tert.butyl-4-hydroxybenzyl-phosphonate, dioctadecyl 3,5-di-tert.butyl-4-hydroxybenzyl-phosphonate and dioctadecyl 5-tert.-butyl-4-hydroxy-3-methylbenzyl-phosphonate.

The following may be mentioned as examples of further additives that can be used together with the stabilizer of this invention and the antioxidant:

1. Aminoaryl derivatives, e.g. phenyl-1-naphthylamine, phenyl-2-naphthylamine, N,N'-diphenyl-p-phenylenediamine, N,N'-di-2-naphthyl-p-phenylenediamine, N,N'-di-naphthyl-p-phenylenediamine, N,N'-di-sec.-butyl-p-phenylenediamine, 6-ethoxy-2,2,4-trimethyl-1,2-dihydroquinoline, 6-dodecyl-2,2,4-trimethyl-1,2-dihydroquinoline, mono- and dioctyliminodibenzyl, polymerized 2,2,4-trimethyl-1,2-dihydroquinoline.

Octylated diphenylamine, nonylated diphenylamine, N-phenyl-N'-cyclohexyl-p-phenylenediamine, N-phenyl-N'-isopropyl-p-phenylenediamine, N,N'-di-sec.octyl-p-phenylene-diamine, N-phenyl-N'-sec.-octyl-p-phenylenediamine, N,N'-di-(1,4-dimethylpentyl)-p-phenylenediamine, N,N'-dimethyl-N,N'-di-(sec.-octyl)-p-phenylenediamine, 2,6-dimethyl-4-methoxyaniline, 4-ethoxy-N-sec.-butylaniline, diphenylamineacetone condensation product, aldol-1-naphthylamine and phenothiazine.

Discoloration effects have to be taken into account when using the above antioxidants.

2. UV-Absorbers and light-stabilising agents 2.1. 2-(2'-Hydroxyphenyl)-benzotriazoles, e.g. the 5'-methyl-, 3',5'-di-tert.-butyl-, 5'-tert.butyl-, 5'-(1,1,3,3-tetramethylbutyl)-, 5-chloro-3',5'-di-tert.-butyl-, 5-chloro-3'-tert.-butyl-5'-methyl-, 3'-sec.-butyl-5'-tert.-butyl-, 3'-alpha-methylbenzyl-5'-methyl-, 3'-alpha-methylbenzyl-5'-methyl-5-chloro-, 4'-hydroxy-, 4'-methoxy-, 4'-octoxy-, 3',5'-di-tert.-amyl-, 3'-methyl-5'-carbomethoxyethyl-, 3',5'-bis(alpha,alpha-dimethylbenzyl),3',5'-bis(alpha,alpha-dimethyl benzyl)-5-chloro-, 3',5'-di-tert.-octylphenyl, 3',5'-di-tert.-octylphenyl-5-chloro- and 5-chloro-3',5'-di-tert.-amyl-derivatives.

2.2. 2,4-bis-(2'-Hydroxyphenyl)-6-alkyl-s-triazines, e.g. the 6-ethyl-, 6-heptadecyl- or 6-undecyl-derivative.

2.3. 2-Hydroxybenzophenones, e.g. the 4-hydroxy-, 4-methoxy-, 4-octoxy-, 4-decyloxy-, 4-dodecyloxy-, 4-benzylozy-, 2',4-4'-trihydroxy- or 2'-hydroxy-4,4'-dimethoxy-dervative.

2.4. 1,3-bis-(2'-Hydroxybenzoyl)-benzenes, e.g. 1,3-bis-(2'-hydroxy-4'-hexyloxy-benzoyl)-benzene, 1,3-bis-(2'-hydroxy-4'-octyloxy-benzoyl)-benzene or 1,3-bis-(2'-hydroxy-4'dodecyloxy-benzoyl)-benzene.

2.5. Esters of optionally substituted benzoic acids, e.g. phenylsalicylate, octylphenylsalicylate, dibenzoylresorcin, bis-(4-tert.-butylbenzoyl)-resorcin, benzoylresorcin, 3,5-di-tert.-butyl-4-hydroxybenzoic acid-2,4-di-tert.-butylphenyl ester or -octadecyl ester or -2-methyl-4,6-di-tert.-butyl ester.

2.6. Acrylates, e.g. α-cyano-β,β-diphenylacrylic acid-ethyl ester or -isooctyl ester, α-carbomethoxy-cinnamic acid methyl ester, α-cyano-β-methyl-p-methoxy-cinnamic acid methyl ester or butyl ester or N-(β-carbomethoxyvinyl)-2-methyl-indoline.

2.7. Sterically hindered amines, e.g. 4-benzoyl-2,2,6,6-tetramethylpiperidine, 4-stearyl-oxy-2,2,6,6-tetramethylpiperidine, bis-(2,2,6,6-tetramethylpiperidyl)-sebacate or 3-n-octyl-7,7,9,9-tetramethyl-1,3,8-triaza-spiro[4,5]decane-2,4-dione.

2.8. Oxalic acid diamides, e.g. 4,4'-di-octyloxy-oxanilide, 2,2'-di-dodecyloxy-5,5'-di-tert.-butyl-oxanilide, 2-ethoxy-2'-ethyl-oxanilide, N,N'-bis-(3-dimethyl-aminopropyl)-oxalamide, 2-ethoxy-5-tert.-butyl-2'-ethyl-5,4'-di-tert.-butyl-oxanilide, or mixtures of ortho- and para-methoxy- as well as of o- and p-ethoxy-disubstituted oxanilides.

3. Metal deactivators, e.g. oxanilide, isophthalic acid dihydrazide, sebacic acid-bis-phenylhydrazide, bis-benzylidene-oxalic acid dihydrazide, N,N'-diacetyl-adipic acid dihydrazide, N,N'-bis-salicyloyloxalic acid dihydrazide, N,N'-bis-salicyloylhydrazine, N,N'-bis-(3,5-di-tert.-butyl-4-hydroxyphenylpropionyl)-hydrazine, N-salicyloyl-N'-salicylalhydrazine, 3-salicyloyl-amino-1,2,4-triazole or N,N'-bis-salicyloyl-thiopropionic acid dihydrazide.

4. Basic co-stabilisers, e.g. alkali metal salts and alkaline-earth metal salts of higher fatty acids, for example Ca-stearate, Zn-stearate, Mg-behenate, Na-ricinoleate or K-plamitate.

5. Nucleation agents, e.g. 4-tert.-butylbenzoic acid, adipic acid or diphenylacetic acid.

6. Phosphites, such as, for example, triphenyl phosphite, diphenylalkyl phosphites, phenyldialkyl phosphites, tri-(nonylphenyl)phosphite, trilauryl phosphite, trioctadecyl phosphite, 3,9-isodecyloxy-2,4,8,10-tetraoxa-3,9-diphospha spiro[5,5]undecane and tri-(4-hydroxy-3,5-di-tert.-butylphenyl)phosphite.

Other additives that can be incorporated in the stabilized compositions are thiosynergists such as dilaurylthiodipropionate or distearylthiodipropionate, lubricants such as stearyl alcohol fillers, carbon black, asbestos, kaolin, talc, glass fibers, pigments, optical brighteners, flameproofing agents and antistatic agents.

The compounds of this invention may be used alone as the sole stabilizer having either mainly an antioxidant function or a light stabilizing function or the stabilizer may combine utility as an antioxidant and light stabilizer. The stabilizers may be used with phenolic antioxidants, lubricants such as calcium stearate, pigments, colorants or dyes, UV absorbers, light stabilizers such as hindered amines, metal deactivators, talc and other fillers, etc.

While the instant compounds can be beneficially used as stabilizers for a variety of substrates both alone and in conjunction with other coadditives, the combination of the instant compounds with selected hindered phenolic antioxidants exhibits enhanced protection of such substrates. The phenolic antioxidants found to be particularly useful are selected from the group consisting of 2,6-di-tert-butyl-4-methylphenol, 4,4'-thio-bis(6-tert.-butyl-3-methylphenol), 2,2'-methylene-bis(6-tert.-butyl-3-methylphenol), 4,4'-methylene-bis-(2,6-di-tert.-butylphenol), 1,1,3-tris(5-tert.-butyl-4-hydroxy-2-methylphenyl)butane, 1,3,5-tris(3,5-di-tert.-butyl-4-hydroxybenzyl)-2,4,6-trimethylbenzene, 2-octylthio-4,6-bis(3,5-di-tert-butyl-4-hydroxyanilino)-s-triazine, n-octadecyl 3,5-di-tert-butyl-4-hydroxyhydrocinnamate, neopentanetetrayl tetrakis(3,5-di-tert.-butyl-4-hydroxy hydrocinnamate), 1,3,5-tris(3,5-di-tert.butyl-4-hydroxybenzyl)isocyanurate, thiodiethylene bis-(3,5-di-tert-butyl-4-hydroxy hydrocinnamate), tris-(2-hydroxyethyl)isocyanurate ester of β-(3,5-di-tert-butyl-4-hydroxyphenyl)propionic acid, 6,6'-ethylidene-bis(2,4-di-tert-.butyl phenol), 6,6'-methylene-bis(2,4-di-tert.butylphenol) and 1,3,5-tris(4-tert.butyl-3-hydroxy-2,6-dimethylbenzyl)isocyanurate.

The compositions comprise (a) a substrate, preferably a polyolefin such as polypropylene, (b) about 0.01 to about 5% by weight of the composition and preferably about 0.025 to about 2%, and most preferably 0.025 to 1% of an instant compound or mixture thereof, and optionally, (c) a phenolic antioxidant or mixture of said antioxidants selected from the group cited directly above and also in a range of 0.01 to 5% and preferably 0.05 to 1%, by weight of the composition.

Likewise, the following light stabilizers are preferred for use, either alone or in conjunction with the listed phenolic antioxidants, as additives for incorporation with the instant stabilizers into the listed substrates: 2-(2'-hydroxy-5'-methylphenyl)benzotriazole; 2-(3',5'-di-tert-butyl-2'-hydroxyphenyl)benzotriazole; 2-(2'-hydroxy-3',5'-di-tert-amylphenyl)benzotriazole; nickel bis[O-ethyl-(3,5-di-tert-butyl-4-hydroxybenzyl)] phosphonate; bis(1,2,2,6,6-pentamethyl-4-piperidyl)-2-n-butyl-2-(3,5-di-tert-butyl-4-hydroxybenzyl)malonate; bis(2,2,6,6-tetramethyl-4-piperidyl)sebacate; dimethylsuccinate polymer with 4-hydroxy-2,2,6,6-tetramethyl-1-piperidinethanol; and polymer of 2,4-dichloro-6-octylamino-s-triazine with N'-(2,2,6,6-tetramethyl-4-piperidyl)hexamethylene diamine.

The following examples further illustrate the embodiments of this invention. In these examples, all parts given are by weight unless otherwise specified.

EXAMPLE 1

6-(N-methylaminoethoxy)-2,4,8,10-tetra-tert-butyl-12H-dibenzo-[d,g][1,3,2]dioxaphosphocin A flame dried flask under nitrogen was charged with 32.3 grams of phosphorus trichloride in 235 ml of dry toluene and with a solution of 100 grams of 2,2'-methylene-bis(4,6-di-tert-butylphenol) and 47.5 grams of triethylamine in 300 ml of dry toluene at a temperature not exceeding 15° C. The reaction was stirred at ambient temperature until the hydroxyl absorption in the IR spectrum disappeared. A solution of 17.6 grams of N-methyl ethanolamine and 23.8 grams of triethylamine was then added. The mixture was heated at 90° C. until the reaction was complete as indicated by TLC. The mixture was filtered, rotary evaporated and chromatographed on silica gel using a mixture of methanol and dichloromethane as eluent and recrystallized from acetonitrile to yield 74.4 g (60%) of white solid m.p. 135°–140° C.

Analysis: Calculated for $C_{32}H_{50}NO_3P$: C, 72.8; H, 9.5; N, 2.6. Found: C, 72.8; H, 9.5; N, 2.6.

EXAMPLE 2

6-(aminoethoxy)-2,4,8,10-tetra-tert-butyl-12H-dibenzo[d,g][1,3,2]dioxaphosphocin A flame dried flask under nitrogen was charged with 0.98 grams of sodium hydride in 100 ml of dry tetrahydrofuran and with 2.5 grams of aminoethanol at ambient temperature until the evacuation of gas was complete. A solution of 20 grams of 2,2'-methylene-bis-[4,6-di-tert-butylphenyl]phosphorochlorodite in 50 ml of dry tetrahydrofuran was then added. The mixture was stirred at ambient temperature until the reaction was complete as indicated by TLC. The mixture was evaporated, triturated with 200 ml of dry toluene and filtered. The resultant filtrate was rotary evaporated and chromatographed on silica gel using a mixture of methanol and dichloromethane as eluent and recrystallized from acetonitrile to yield 4.2 g (20%) of white powder m.p. 216°–221° C.

Analysis Calculated for $C_{31}H_{48}NO_3P$: C, 72.5; H, 9.4; N, 2.7; P, 6.0. Found: C, 72.7; H, 9.8; N, 2.9; P, 5.9.

EXAMPLE 3

2,2'-Bis(2,4,8,10-tetra-tert-butyl-12H-dibenzo[d,g][1,3,2]dioxa-phosphocin-6-yl-6-oxy)-diethylamine The procedure of Example 1 was repeated using 27.47 grams of phosphorus trichloride, 84.93 grams of 2,2'-methylenebis(4,6-di-tert-butylphenol), 10.51 grams diethanolamine, and 60.72 grams triethylamine. The product was recrystallized from 2-butanone:toluene and toluene:acetonitrile to give 12.0 grams white solid, m.p. 226°–232° C.

Analysis Calculated for $C_{62}H_{93}NO_6P_2$: C, 73.7; H, 9.3; N, 1.4. Found: C, 74.2; H, 9.1; N, 1.4.

EXAMPLE 4

2,2'-Bis(2,4,8,10-tetra-tert-butyl-dibenzo[d,f][1,3,2]dioxaphosphepin-6-yl-6-oxy)-diethylamine The procedure of Example 1 was repeated using 27.47 grams of phosphorus trichloride, 82.13 grams of 3,3',5,5'-tetra-tert-butylbiphenyl-2,2'-diol, 10.51 grams diethanolamine, and 60.72 grams triethylamine. The product was purified by flash chromatography to give a white solid m.p. 96°–100° C.

Analysis: Calculated for $C_{60}H_{89}NO_6P_2$: C, 73.4; H, 9.1; N, 1.4. Found: C, 73.4, H, 9.3; N, 1.3.

EXAMPLE 5

6-[2'-(tert-butylamino)ethoxy]-2,4,8,10-tetra-tert-butyl-dibenzo[d,f][1,3,2]dioxaphosphepin The procedure of Example 1 was repeated using 6.87 grams phosphorous trichloride, 20.53 grams 3,3',5,5'-tetra-tert-butyl-biphenyl-2,2'-diol, 5.86 grams N-tert-butylaminoethanol and 15.18 grams triethylamine. The product was recrystallized twice from acetonitrile to give 17.74 grams (64% yield) of white solid m.p. 135°–138° C.

Analysis: Calculated for $C_{34}H_{34}NO_3P$: C, 73.5; H, 9.8; N, 2.5. Found: C, 74.1; H, 9.7; N, 2.5.

EXAMPLE 6

6-[2'-(tert-butylamino)ethoxy]-2,4,8,10-tetra-tert-butyl-12-methyl-12H-dibenzo[d,g][1,3,2]dioxaphosphocin The procedure of Example 1 was repeated using 27.47 grams phosphorus trichloride, 87.74 grams 2,2'-ethylidenebis-(4,6-di-tert-butylphenol), 23.44 grams N-tert-butylamino-ethanol, and 60.72 grams triethylamine. The product was recrystallized twice from 2-butanone to give 43.93 grams white solid m.p. 174°–175° C.

Analysis Calculated for $C_{36}H_{58}NO_3P$: C, 74.1; H, 10.0; N, 2.4. Found: C, 74.4; H, 9.7; N, 2.4.

EXAMPLE 7

6-[2'-(tert-butylamino)ethoxy]-2,4,8,10-tetra-tert-butyl-12H-di-benzo[d,g][1,3,2]dioxaphosphocin The procedure of Example 1 was repeated using 27.47 grams phosphorus trichloride, 84.93 grams 2,2'-methylenebis (4,6-di-tert-butylphenol), 23.44 grams N-tert-butylaminoethanol, and 60.72 grams triethylamine. The product was recrystallized from acetone to give 59.48 grams (52% yield) white solid m.p. 189°–192° C.

Analysis Calculated for $C_{35}H_{56}NO_3P$: C, 73.8; H, 9.9; N, 2.5. Found: C, 74.0; H, 9.8; N, 2.5.

EXAMPLE 8

Processing Stability of Polypropylene

| Base Formulation | |
| --- | --- |
| Polypropylene* | 100 parts |
| Calcium Stearate | 0.10 parts |

*Profax 6801 from Hercules Chemical

Stabilizers were solvent blended into polypropylene as solutions in methylene chloride and, after removal of the solvent by evaporation at reduced pressure, the resin was extruded using the following extruder conditions:

| Temperature (°C.) | |
| --- | --- |
| Cylinder #1 | 260 |
| Cylinder #2 | 274 |
| Cylinder #3 | 288 |
| Die #1 | 288 |
| Die #2 | 288 |
| Die #3 | 288 |
| RPM | 100 |

During extrusion, the internal extruder pressure was determined using a pressure transducer. After each of the first, third and fifth extrusions, resin pellets were compression molded into 125 mil (3.2 mm) thick plaques at 193° C. and specimen yellowness index (Y.I.) determined according to ASTM D1925-63T. The results are tabulated in the following table:

| | Extrusion Temperature 288° C. | | | | | |
|---|---|---|---|---|---|---|
| | Transducer Pressure After Extrusion (psi) | | | YI Color After Extrusion | | |
| Additives | 1 | 3 | 5 | 1 | 3 | 5 |
| None | 1350 | 1150 | 1000 | 5.1 | 7.6 | 9.2 |
| 0.1% Ex. 3 | 1575 | 1450 | 1300 | 4.9 | 6.5 | 7.9 |
| 0.1% Ex. 4 | 1550 | 1450 | 1250 | 5.1 | 5.6 | 6.6 |
| 0.1% Ex. 7 | 1550 | 1425 | 1350 | 5.2 | 5.9 | 7.4 |
| 0.1% Antioxidant A* | 1450 | 1350 | 1275 | 12.1 | 17.4 | 19.5 |
| 0.1% Antioxidant A* + 0.05% Ex. 4 | 1550 | 1475 | 1425 | 10.7 | 15.4 | 18.2 |

*Neopentyltetrayl tetrakis [3-(3',5'-di-tert-butyl-4'-hydroxyphenyl) propionate]

EXAMPLE 9

The procedure of Example 8 was identically repeated with the exception that the following base formulation and extruder conditions were utilized.

| Base Formulation | |
|---|---|
| Polypropylene* | 100 parts |
| Calcium Stearate | 0.10 parts |

*Profax 6501 from Hercules Chemical

| Extruder Conditions | |
|---|---|
| | Temperature (°C.) |
| Cylinder #1 | 232 |
| Cylinder #2 | 246 |
| Cylinder #3 | 260 |
| Die #1 | 260 |
| Die #2 | 260 |
| Die #3 | 260 |
| RPM | 100 |

The results are tabulated in the following table:

| | Extrusion Temperature 260° C. | | | | | |
|---|---|---|---|---|---|---|
| | Transducer Pressure After Extrusion (psi) | | | YI Color After Extrusion | | |
| Additives | 1 | 3 | 5 | 1 | 3 | 5 |
| None | 530 | 470 | 450 | 3.8 | 5.8 | 8.0 |
| 0.1% Antioxidant A* + 0.05% Ex. 4 | 645 | 620 | 570 | 3.1 | 5.3 | 7.5 |
| 0.1% Antioxidant A* + 0.05% Ex. 7 | 665 | 605 | 540 | 3.6 | 2.0 | 9.2 |

*Neopentyltetrayl tetrakis [3-(3',5'-di-tert-butyl-4'-hydroxyphenyl) propionate]

Summarizing, it is seen that this invention provides novel cyclic phosphite compounds which exhibit effective stabilization activity. Variations may be made in proportions, procedures and materials without departing from the scope of the invention as defined by the following claims.

EXAMPLE 10

Reactivity with Isocyanates

The instant phosphites having at least one hydrogen on the nitrogen atom provide an active site for reaction with reactive end groups of polymers such as isocyanate groups.

The differences between the primary or secondary amino groups of the instant phosphites and the tertiary amino groups of the prior art phosphites are illustrated using butyl isocyanate as a model for a urethane prepolymer having isocyanate groups in order to facilitate obtaining appropriate spectroscopic data.

Test Compounds

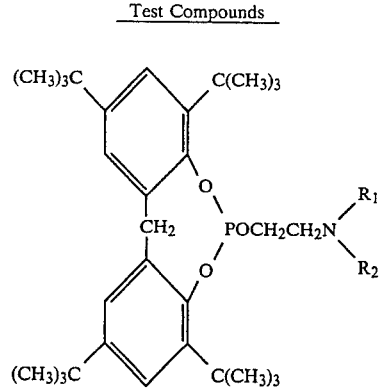

| Compound | $R_1$ | $R_2$ |
|---|---|---|
| #1 - primary aminoalkylphosphite | H | H |
| #2 - secondary aminoalkylphosphite | H | $CH_3$ |
| #3 - tertiary aminoalkylphosphite | $C_2H_5$ | $C_2H_5$ |

Test Procedure

The following test was conducted in order to determine that the terminal NH functionality is a reactive nitrogen site which allows for chemical incorporation into a polymer during cure. Butyl isocyanate was utilized as a model for a urethane prepolymer to reflect the reactive effect with an isocyanate functionality. The butyl isocyanate was utilized instead of a urethane prepolymer because of the difficulty in obtaining spectroscopic data in high molecular weight prepolymers.

The aminoalkyl phosphites were mixed with an equivalent of butyl isocyanate. Additionally, 0.25 ml of tetrahydrofuran (THF) was added as a reaction medium.

| 1° Formulation | |
|---|---|
| compound #1 | 0.51 g |
| n-butyl isocyanate | 0.01 g |
| THF | 0.25 ml |
| 2° Formulation | |
| compound #2 | 0.52 g |
| n-butyl isocyanate | 0.01 g |
| THF | 0.25 ml |
| 3° Formulation | |
| compound #3 | 0.56 g |
| n-butyl isocyanate | 0.01 g |
| THF | 0.25 ml |

The ingredients of the formulations were mixed for five minutes and then the volatiles were removed in vacuo. Infrared (IR) spectra (1% solution in $CCl_4$) were then obtained. Unreacted n-butyl isocyanate and aminoalkyl phosphites were run as controls.

| Sample | IR Spectra (cm$^{-1}$) | | | Comments |
|---|---|---|---|---|
| | —NCO | C=O | POC Aliphatic Stretch | |
| 1° Formulation | 1180 weak* | 1685 strong | 1040 strong | Exothermic |
| 2° Formulation | 2280 weak* | 1665 strong | 1020 strong | Exothermic |
| 3° Formulation | 2280 weak* | None | 1020 strong | — |
| n-butyl isocyanate | 2280 intense | None | None | — |
| compound #1 | None | None | 1000 strong | — |
| compound #2 | None | None | 1040 strong | — |
| compound #3 | None | None | 1020 strong | — |

*trace residual n-butyl isocyanate.

Conclusions:

1. The primary and secondary aminoalkyl phosphites undergo an exothermic reaction with an isocyanate to produce ureas as indicated by the formation of a carbonyl absorption between 1665–1685 cm$^{-1}$.
2. The tertiary aminoalkyl phosphite does not react with isocyanates as evidenced by the absence of carbonyl absorption.
3. The primary and secondary aminoalkyl phosphites retain their phosphite moiety intact as evidenced by the presence of a POC aliphatic stretch near 1020 cm$^{-1}$ in the IR spectra after reaction.

The results clearly reveal that the terminal substituents of the instant compounds are not merely innocuous nitrogenous portions as a terminal non-reactive substituent but, rather, provide reactive nitrogen sites which facilitate chemical incorporation into a polymer during cure. These data are clear in this regard. Thus, the primary and secondary aminoalkyl phosphites experienced an exothermic reaction with the isocyanate to produce ureas as indicated by the formation of the carbonyl absorption. In contrast, the tertiary aminoalkyl phosphite did not undergo such a reaction. Finally, the phosphite moiety was maintained intact in all of these compounds, thereby indicating that the reaction which took placed involved the terminal nitrogen site.

It is clear that the instant primary and secondary phosphites which can be chemically bonded via a urea linkage to the polyurethane would be in a better position to provide enhanced stabilization to the polyurethane than a tertiary phosphite of the prior art merely admixed in the polyurethane, but not bonded thereto.

EXAMPLE 11

Stabilization of Epoxy Resin Coatings Against Yellowing

Epoxy resin/polyamide coatings are widely used as industrial maintenance paints although they tend to yellow on outdoor exposure.

The incorporation of ultraviolet light absorbers and other additives into said coatings reduces this tendency to yellow while not adversely affecting cured resin properties.

A "1"-type epoxy resin coating composition having the following components in parts by weight is used as a control.

| "1" type Expoxy resin* | 143 |
|---|---|
| titanium dioxide (R-960) duPont | 181 |
| xylene/cellosolve/methyl isobutyl ketone 100/62.5/83 | 65 |
| urea/formaldehyde Beetle 216-8 (American Cyanamid) | 5 |
| polyamide hardener HZ815 X-70 (CIBA-GEIGY) | 80 |

*epoxy resin based on diglycidyl bisphenol A dissolved at 70% by weight level in xylene/cellosolve and having an epoxy value of 0.209 eq/100 grams.

The pigmented coating compomposition is coated on a metallic panel and cured by heating at 204° C. for 10 minutes.

The yellowness index (YI) is measured on a Tristimulus Colorimeter according to ASTM D 1925 on the cured coating before and then after exposure for 200 hours in a CI-65 Xenon Arc Weather-O-meter. The change in YI is an indication of the amount of discoloration or yellowing occurring as a result of the exposure to ultraviolet light. (Higher YI values mean more yellowing or discoloration.)

The same epoxy resin formulation is also prepared and cured which contains additionally (% by weight based on total solids) a hindered amine plus benzotriazole; the same hindered amine and benzotriazole plus a tertiary amino phosphite (A); or plus a secondary amino phosphite (B).

Yellowness index values are also obtained for these three stabilized cured coatings as well. Results are given in the table which follows.

Test Compounds (CH$_3$)$_3$C, C(CH$_3$)$_3$, (CH$_3$)$_3$C, C(CH$_3$)$_3$ substituted bisphenol structure with X bridge and POCH$_2$CH$_2$N(T$_1$)(T$_2$) group

| Compound | X | T$_1$ | T$_2$ |
|---|---|---|---|
| A, tertiary amino phosphite | direct bond | E | E |
| B, secondary amino phosphite (compound of Example 7) | methylene | H | tert-butyl |

E is

-continued

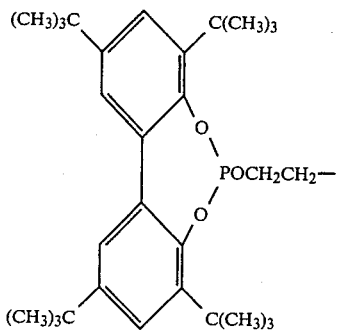

| Stabilizer Additives (% by wght) | Initial Yellowness Index (YI) | Yellowness Index after Exposure* | Change in YI | % Improvement over Control |
|---|---|---|---|---|
| None | 2.5 | 11.1 | 8.6 | — |
| no phosphite** | 2.7 | 7.7 | 5.0 | 42 |
| A, tertiary amino phosphite (1%)** | 3.0 | 7.7 | 4.7 | 45 |
| B, secondary amino phosphite (1%)** | 2.9 | 6.7 | 3.8 | 56 |

*Coating exposed for 200 hours in Cl-65 Xenon Arc Weather-O-Meter
**Each coating also contains 2% by weight of 2-(2-hydroxy-,3,5-di-tert-amyl-phenyl)-2H—benzotriazole and 2% by weight of bis(1,2,2,6,6-pentamethyl-4-piperidinyl) sebacate.

These data indicate that use of a combination of a hindered amine plus benzotriazole improves resistance to discoloration of the cured epoxy resin exposed to ultraviolet light.

The additional presence of the tertiary amino phosphite (A) provides a marginal improvement (1.06x) over that obtained by use of the hindered amine plus benzotriazole.

However, the additional presence of the instant secondary amino phosphite (B) provides a quite discernible improvement (1.32x) over that obtained by use of the hindered amine plus benzotriazole or (1.24x) over that obtained by use of the hindered amine plus benzotriazole plus tertiary amino phosphite.

What is claimed is:

1. A compound of the formula

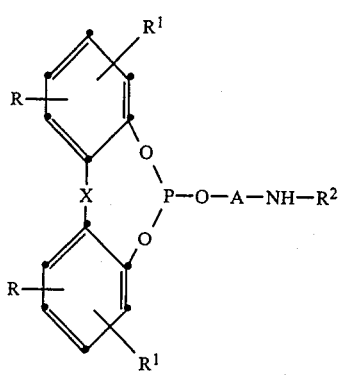

wherein
R and $R^1$ independently are hydrogen, alkyl of 1 to 18 carbon atoms, cycloalkyl of 5 to 6 carbon atoms, phenyl or phenyl substituted with alkyl of 1 to 18 carbon atoms;

A is alkylene of 1 to 6 carbon atoms or cycloalkylene of 5 to 6 carbon atoms;
X is a direct bond or alkylidene of 1 to 12 carbon atoms; and
$R^2$ is hydrogen, alkyl of 1 to 12 carbon atoms or the group

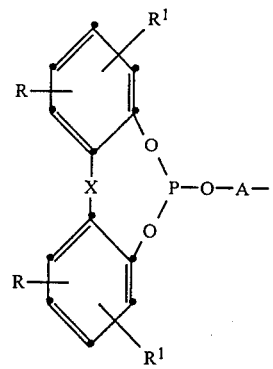

2. A compound of claim 1, wherein R is in the ortho position to the phosphite oxygen in each of the phenyl rings.

3. A compound of claim 2, wherein R is alkyl of 4 to 8 carbon atoms.

4. A compound of claim 3, wherein $R^1$ is tert.-butyl tert.pentyl or tert.octyl.

5. A compound of claim 2, wherein $R^1$ is tert.-alkyl of from 4 to 8 carbon atoms.

6. A compound of claim 2, wherein X is alkylidene of the formula

wherein $R^3$ and $R^4$ are independently hydrogen or alkyl of 1 to 7 carbon atoms, provided that the total number of carbon atoms does not exceed 12.

7. A compound of claim 1, wherein $R^2$ is hydrogen, alkyl of 1 to 4 carbon atoms or the group

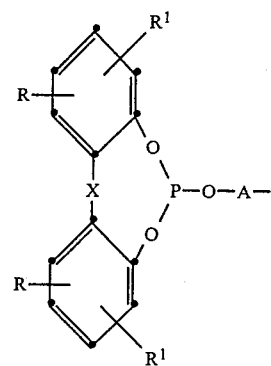

8. 6-(N-methylaminoethoxy)-2,4,8,10-tetra-tert-butyl-12H-dibenzo[d,g][1,3,2]dioxaphosphocin according to claim 2.

9. 6-(aminoethoxy)-2,4,8,10-tetra-tert-butyl-12H-dibenzo[d,g][1,3,2]dioxaphosphocin according to claim 2.

10. 2,2'-Bis(2,4,8,10-tetra-tert-butyl-12H-dibenzo[d,g][1,3,2]dioxaphosphocin-6-yl-6-oxy)-diethylamine according to claim 2.

11. 2,2'-Bis(2,4,8,10-tetra-tert-butyl-dibenzo[d,f][1,3,2]dioxaphosphepin-6-yl-6-oxy)-diethylamine according to claim 2.

12. 6-[2'-(tert-butylamino)ethoxy]-2,4,8,10-tetra-tert-butyl-dibenzo[d,f][1,3,2]dioxaphosphepin according to claim 2.

13. 6-[2'-(tert-butylamino)ethoxy]-2,4,8,10-tetra-tert-butyl-12-methyl-12H-dibenzo[d,g][1,3,2]dioxaphosphocin according to claim 2.

14. 6-[2'-(tert-butylamino)ethoxy]-2,4,8,10-tetra-tert-butyl-12H-dibenzo[d,g][1,3,2]dioxaphosphocin according to claim 2.

15. A composition of matter comprising an organic material subject to oxidative, thermal and actinic degradation stabilized with an effective stabilizing amount of a compound of claim 1.

16. A composition of claim 15, wherein the organic material is a synthetic polymer.

17. A composition of claim 16, wherein said synthetic polymer is a polyolefin homopolymer or copolymer.

18. A composition of claim 17, wherein said polyolefin is selected from the group consisting of polyethylene, polypropylene, polyisobutylene, poly(butene-1), poly(pentene-1), poly(methylbutene-1) and poly(4-methylpentene-1).

19. A composition of claim 16, wherein said polymer is selected from the group consisting of polystyrene, acrylonitrile/butadiene/styrene, styrene/butadiene rubber, polyesters, polyurethanes, polycarbonates, polyamides and polysulfones.

20. A composition of claim 15 which also contains a phenolic antioxidant selected from the group consisting of 2,6-di-tert-butyl-4-methylphenol, 4,4'-thio-bis(6-tert-butyl-3-methylphenol), 2,2'-methylene-bis(6-tert-butyl-3-methylphenol, 4,4'-methylene-bis(2,6-di-tert-butylphenol), 1,1,3-(5-tert-butyl-4-hydroxy-2-methylphenyl)-butane, 1,3,5-tris(3,5-di-tert-butyl-4-hydroxybenzyl)-2,4,6-trimethylbenzene, 2-octylthio-4,6-bis(3,5-di-tert-butyl-4-hydroxy-anilino)-s-triazine, n-octadecyl 3,5-di-tert-butyl-4-hydroxy-hydrocinnamate, neopentane-tetrayl tetrakis(3,5-di-tert-butyl-4-hydroxy-hydrocinnamate), 1,3,5-tris(3-tert-butyl-4-hydroxybenzyl) isocyanurate, thiodiethylene bis(3,5-di-tert-butyl-4-hydroxyhydrocinnamate), tris(2-hydroxyethyl)isocyanurate ester of β-(3,5-di-tert-butyl-4-hydroxyphenyl)propionic acid 6,6'-ethylidene-bis(2,4-di-tert-butylphenol), 6,6'-methylene-bis(2,4-di-tert-butylphenol) and 1,3,5-tris(4-tert-butyl-3-hydroxy-2,6-dimethylbenzyl) isocyanurate.

21. A composition of claim 15 which also contains a light stabilizer selected from the group consisting of 2-(2'-hydroxy-5'-methylphenyl)benzotriazole; 2-(3',5',di-tert-butyl-2'-hydroxyphenyl)benzotriazole; 2-(2'-hydroxy-3',5'-di-tert-amylphenyl)benzotriazole; nickel bis[O-ethyl-(3,5-di-tert-butyl-4-hydroxybenzyl)]-phosphonate; bis(1,2,2,6,6-pentamethyl-4-piperidyl)-2-n-butyl-2-(3,5-di-tert-butyl-4-hydroxybenzyl)malonate; bis(2,2,6,6-tetramethyl-4-piperidyl) sebacate; bis(1,2,2,6,6-pentamethyl-4-piperidinyl) sebacate; dimethyl-succinate polymer with 4-hydroxy-2,2,6,6-tetramethyl-1-piperidinethanol; and polymer of 2,4-dichloro-6-octylamino-s-triazine with N'-(2,2,6,6-tetramethyl-4-piperidyl)hexamethylene diamine.

22. A composition of claim 20 which also contains a light stablizer selected from the group consisting of 2-(2'-hydroxy-5'-methylphenyl)benzotriazole; 2-(3',5'-di-tert-butyl-2'-hydroxyphenyl)benzotriazole; 2-(2'-hydroxy-3,'5'-di-tert-amylphenyl)benzotriazole; nickel bis[O-ethyl-(3,5-di-tert-butyl-4-hydroxybenzyl)]phosphonate; bis(1,2,2,6,6-pentamethyl-4-piperidyl)-2-n-butyl-2-(3,5-di-tert-butyl-4-hydroxybenzyl)malonate; bis(2,2,6,6-tetramethyl-4-piperidyl) sebacate; bis(1,2,2,6,6-pentamethyl-4-piperidinyl) sebacate; dimethyl-succinate polymer with 4-hydroxy-2,2,6,6-tetramethyl-1-piperidinethanol; and polymer of 2,4-dichloro-6-octylamino-s-triazine with N'-(2,2,6,6-tetramethyl-4-piperidyl)hexamethylene diamine.

23. A method for stabilizing an organic material against oxidative, thermal and actinic degradation which comprises incorporating into said organic material an effective stabilizing amount of a compound of claim 1.

24. A composition of claim 15 wherein said polymer is selected from the group consisting of polyurethanes, polyesters, polyamides and epoxy resins.

25. A composition of claim 24 wherein the polymer is a polyurethane or epoxy resin.

* * * * *